(12) United States Patent
Kim et al.

(10) Patent No.: US 10,463,706 B2
(45) Date of Patent: Nov. 5, 2019

(54) METHOD OF PREPARING AKEBIA QUINATA EXTRACT AND FUNCTIONAL FOOD USING THE SAME

(71) Applicant: Song Bae Kim, Gongju-si, Chungcheongnam-do (KR)

(72) Inventors: Song Bae Kim, Gongju-si (KR); Jong-Seok Kim, Gyeryong-si (KR); Hye-Yeong Kim, Gyeryong-si (KR); Jong-Uk Kim, Gongju-si (KR); Tae-Dong Kim, Daejeon (KR)

(73) Assignee: Song Bae Kim, Gongju-si (KR)

( * ) Notice: Subject to any disclaimer, the term of this patent is extended or adjusted under 35 U.S.C. 154(b) by 34 days.

(21) Appl. No.: 15/464,799

(22) Filed: Mar. 21, 2017

(65) Prior Publication Data
US 2017/0290868 A1   Oct. 12, 2017

(30) Foreign Application Priority Data
Apr. 12, 2016 (KR) .......................... 10-2016-0044924

(51) Int. Cl.
| A61K 36/00 | (2006.01) |
| A61K 36/185 | (2006.01) |
| A23L 33/105 | (2016.01) |
| A61K 9/00 | (2006.01) |
| A61K 9/20 | (2006.01) |
| A61K 9/48 | (2006.01) |
| A61K 31/704 | (2006.01) |
| A61K 36/9068 | (2006.01) |

(52) U.S. Cl.
CPC .......... *A61K 36/185* (2013.01); *A23L 33/105* (2016.08); *A61K 9/0056* (2013.01); *A61K 9/20* (2013.01); *A61K 9/48* (2013.01); *A61K 31/704* (2013.01); *A61K 36/9068* (2013.01); *A23V 2002/00* (2013.01); *A61K 2236/10* (2013.01); *A61K 2236/333* (2013.01); *A61K 2236/50* (2013.01); *A61K 2236/53* (2013.01)

(58) Field of Classification Search
None
See application file for complete search history.

(56) References Cited

FOREIGN PATENT DOCUMENTS

| CN | 101590086 | 12/2009 |
| JP | 2010148425 | 7/2010 |
| JP | 2014111652 | 6/2014 |
| KR | 10-2005-0087498 | 8/2005 |
| KR | 100826902 | 5/2008 |
| WO | WO-2004069263 A1 * | 8/2004 ........... A61K 36/185 |

OTHER PUBLICATIONS

Lu et al. (2013) Afr. J. Tradit Complement Altern Med. 10(5): 313-317. (Year: 2013).*
Choi et al. (2005) J. Med. Food 8(1): 78-85 (Year: 2005).*
Ghayur et al. (2005) Vascular Pharmacology, 43: 234-241. (Year: 2005).*
Wu et al. (2001) Ultrasonics Sonochemistry 8: 347-352. (Year: 2001).*
Kang et al. (2010) Korean J. Food Preserv. vol. 17, No. 3. pp. 311-319. (Year: 2010).*
Jiang, D. et la., Triterpene Saponins from the Fruits of Akebia Quinata, Biochem. Syst. Ecol. 2008, vol. 36, pp. 138-141.
Azmir, J. et al., Techniques for Extraction of Bioactive Compounds from Plant Materials: A Review, J. Food Eng., 2013 vol. 117, pp. 426-436.
Li, H. et al., Effects of Ultrasound on Extraction of Saponin from Ginseng, Jpn. J. Appl. Phys., 1994, vol. 33, pp. 3085-3087.

* cited by examiner

*Primary Examiner* — Russell G Fiebig
(74) *Attorney, Agent, or Firm* — Hauptman Ham, LLP

(57) ABSTRACT

Provided are a method of extracting saponin which is the physiologically active component of *Akebia quinata* with high efficiency, by sequentially subjecting to a) adding *Akebia quinata* flesh to *Akebia quinata* seeds and performing aging; and b) extracting with alcohol, a method of further improving saponin extraction efficiency by adding ginger, and a food composition containing the extract produced by this method. Higher added value may be created by improving the saponin extraction efficiency from *Akebia quinata* seeds using *Akebia quinata* flesh which has not been utilized when extracting saponin.

3 Claims, No Drawings

METHOD OF PREPARING AKEBIA QUINATA EXTRACT AND FUNCTIONAL FOOD USING THE SAME

CROSS-REFERENCE TO RELATED APPLICATIONS

This application claims priority under 35 U.S.C. § 119 to Korean Patent Application No. 10-2016-0044924, filed on Apr. 12, 2016 in the Korean Intellectual Property Office, the disclosure of which is incorporated herein by reference in its entirety.

TECHNICAL FIELD

The following disclosure relates to a method of extracting an effective component contained in *akebia quinata* seeds with improved efficiency, and a functional food using the same.

BACKGROUND

Presently, people are suffering from various diseases such as cancer, weakened immunity, adult diseases, gastrointestinal diseases, hypertension, diabetes, cardiovascular diseases and fatigue accumulation, due to polluted atmosphere quality and westernized dietary, drinking, stress, irregular meals and the like. Accordingly, as interest in the prevention and treatment of the above diseases increases, demand of health functional food therefor is also increasing. In particular, recently, interest in vitamins, mineral preparations, as well as food processed from natural materials without side effect even in long-term use, or health functional food using a natural material extract is more increasing.

Among the effective components of this health functional food, attention is especially drawn to saponin. Saponin is a generic name of triterpene or steroid-based glycoside distributed in the vegetable kingdom, and a natural surfactant substance having a bubbling characteristic. Saponin is commonly known as an effective component of ginseng and red ginseng, but also present in many plants such as beans, spring onion, deodeok, balloonflower, water dropwort, garlic, onion and kadzu, and also contained in *Akebia quinata* seeds in a large amount. Saponin has a function to decrease cholesterol and increase immunity, and is known to represent various pharmacological active effects such as prevention and treatment of cardiovascular diseases, an immunity enhancement effect, an anti-cancer effect, inflammation relief, diabetes inhibition, prevention of atherosclerosis and hypertension, liver function promotion, fatigue recovery, antioxidant activity and anti-inflammatory activity.

*Akebia quinata* is a vine belonging to Anthophyta class/Ranunculales order/Lardizabalaceae family/*Akebia* genus, and distributed throughout Korea, Japan, China, etc. The scientific name thereof is *akebia quinata*, and it is also called Imhabuin (林下婦人), Moktong (木通) or Tongcho (通草), and the *Akebia quinata* fruit is also called Yeonbokja (燕覆子). It mainly inhabits valleys or gorge, and grows by winding up a neighboring tree, or leaning against a rock. Since its leaves and fruits have an unusual shape, it is also used for landscaping, and its roots, stem and fruits are all edible. It bears fruits in September or October, and the flesh of the fruits has a curved oval shape, a length of 6 to 10 cm, and a very thick skin. It is characterized in that when the fruit is fully ripe, the skin is split so that a white and soft content and black seeds come out. The stem and root are collected during autumn, dried in the shade, and then boiled for drinking tea, and the fruit is collected when ripe during autumn, and used raw, or dried in the shade to be boiled for drinking tea. In addition, young leaves are blanched for eating a seasoned vegetable, and ripe fruits are also eaten as they are.

The stem and roots of *Akebia quinata* are used as medicinal materials in oriental medicine, and known to have diuretic, antibacterial, and anti-inflammatory effects. The *Akebia quinata* fruit contains effective components such as saponin and oleanolic acid, and in particular, saponin is more contained in the seed than in the stem or root.

Korean Patent Registration No. 10-0573375 provides a composition having an anticancer activity by utilizing an *Akebia quinata* seed extract, but saponin contained in the *Akebia quinata* seed was not sufficiently utilized. Further, the study for utilizing the stem and root of *Akebia quinata* was actively performed with the influence of oriental medicine, however, the study of the *Akebia quinata* fruit was insufficient, as compared with the stem or root. Thus, the present inventors improved the saponin extraction efficiency from *Akebia quinata* seeds by various studies, and have developed functional food by using it.

RELATED ART DOCUMENT

Patent Document

Korean Patent Registration No. 10-0573375

SUMMARY

An embodiment of the present invention is directed to providing a method of preparing an *Akebia quinata* extract having improved saponin extraction efficiency.

Another embodiment of the present invention is directed to providing food using an *Akebia quinata* extract having a high saponin content to have a more improved function.

In one general aspect, a method of preparing an *Akebia quinata* extract includes:

a) aging a raw material including *Akebia quinata* seeds and *Akebia quinata* flesh; and b) extracting an extract containing saponin as an effective component from the aged raw material by using an alcohol extraction solution.

The raw material may include 0.5 to 5 parts by weight of the *Akebia quinata* flesh, based on 1 part by weight of the *Akebia quinata* seeds.

The temperature in the aging step may be 20 to 60° C.

The raw material may include 0.05 to 0.2 parts by weight of ginger, based on 1 part by weight of the *akebia quinata* seeds.

The raw material may further include one or two or more additives selected from the group consisting of ginseng, wild ginseng, balloonflower, deodeok, kadzu and yam.

In the extraction according to the present invention, step b) may specifically include:

b1) adding an alcohol extraction solution to the raw material aged in step a), and performing ultrasonic irradiation; and b2) centrifuging a product from step b1) and recovering a supernatant liquid to prepare a first extract.

Further, the residue from which the supernatant liquid is removed in step b2) may be used as the raw material of step a), and steps b1) and b2) may be repeated twice or more.

In step b1), the ultrasonic irradiation may be performed for 20 to 60 minutes.

In another general aspect, functional food includes the extract prepared according to the method of the present invention.

Other features and aspects will be apparent from the following detailed description, the drawings, and the claims.

DETAILED DESCRIPTION OF EMBODIMENTS

The advantages, features and aspects of the present invention will become apparent from the following description of the embodiments with reference to the accompanying drawings, which is set forth hereinafter. The present invention may, however, be embodied in different forms and should not be construed as limited to the embodiments set forth herein. Rather, these embodiments are provided so that this disclosure will be thorough and complete, and will fully convey the scope of the present invention to those skilled in the art. The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Hereinafter, the present invention will be described in detail by the Examples. However, the following Examples and Preparation Examples are only illustrative of the present invention, and do not limit the present invention in any way. Further, the terms used in the present invention are based on common knowledge of a general skilled person in the art, unless otherwise defined, and the description of the technique well known in the art obscuring the essence of the invention will be omitted.

"*Akebia quinata*" in the present invention is the scientific name, and the fruits, flesh, rind and seeds thereof refer to those collected as ripe ones in the harvest season.

The present applicant studied for a long time in order to improve extraction efficiency of saponin contained in *Akebia quinata* seeds, and as a result, found out that in the case of aging *Akebia quinata* flesh containing little saponin and *Akebia quinata* seeds together and performing extraction, the saponin extraction efficiency from *akebia quinata* seeds is significantly increased. Furthermore, in the case of aging *Akebia quinata* seeds and *Akebia quinata* flesh together and preparing an extract, improved sensitivity such as decreased bitterness and improved refreshing feeling was shown.

The method of preparing an *Akebia quinata* extract according to the present invention may include:

a) aging a raw material including *Akebia quinata* seeds and *Akebia quinata* flesh; and b) extracting an extract containing saponin as an effective component from the aged raw material by adding an alcohol extraction solution.

As described above, in the seeds, rind, skin, flesh and the like of *akebia quinata*, saponin is present in the seeds, and rarely contained in other parts of *akebia quinata*. Accordingly, when extracting saponin contained in *akebia quinata*, it is common to extract saponin from the *Akebia quinata* seeds.

However, in the case of extracting saponin using the *Akebia quinata* seeds, there is a limitation on the extraction efficiency, and thus, though saponin is present in *Akebia quinata* seeds in a large amount, saponin contained in *Akebia quinata* seeds may not be sufficiently utilized, due to low extraction efficiency, and discarded.

As described above, the present applicant studied for a long time in order to improve the extraction efficiency of saponin contained in *Akebia quinata* seeds, and as a result, it has been surprisingly found that though saponin is rarely present in *Akebia quinata* flesh, by adding *akebia quinata* flesh to *Akebia quinata* seeds and carrying out aging, the extraction efficiency of saponin contained in the *Akebia quinata* seeds may be significantly improved. Substantially, when adding *Akebia quinata* flesh to *akebia quinata* seeds and performing aging and then extraction, the extraction efficiency may be improved by at most up to 170%, as compared with the case of extraction by aging only *Akebia quinata* seeds. Cause of this phenomenon has not been clearly revealed, but it is assumed that a certain component of *Akebia quinata* flesh destroys a cell membrane of *Akebia quinata* seeds to improve the extraction efficiency of saponin.

The *Akebia quinata* seeds or *Akebia quinata* flesh of the present invention may be dried powder, or those being crushed or cut into pieces, but not limited thereto. Further, the extraction from *Akebia quinata* according to the present invention may be performed by mixing *akebia quinata* seeds and flesh, or using *Akebia quinata* fruits themselves.

According to an exemplary embodiment of the present invention, the raw material may contain 0.5 to 5 parts by weight, preferably 0.7 to 2 parts by weight, more preferably 0.9 to 1.5 parts by weight of the *Akebia quinata* flesh, based on 1 part by weight of the *Akebia quinata* seeds. In order to show improvement of saponin extraction efficiency, it is preferred to add 0.5 parts by weight of the *Akebia quinata* flesh, based on 1 part by weight of the *Akebia quinata* seeds, and when too much flesh is added, the extraction efficiency from the *Akebia quinata* seeds is not further improved, and the extraction may be interrupted, and thus, it is preferred to add less than 5 parts by weight of the flesh, based on 1 part by weight of the *Akebia quinata* seeds.

In addition, the raw material of the present invention may further contain ginger as an additive for improving extraction efficiency from *Akebia quinata* seeds and flesh. In order to more improve the saponin extraction efficiency from the *Akebia quinata* seeds, various additives were added and the effect of the additives on the extraction efficiency from *Akebia quinata* seeds was examined, and as a result, it has been surprisingly found out that when further adding ginger to perform aging and extraction, the saponin extraction efficiency from *akebia quinata* seeds is further improved. As described above, by aging *Akebia quinata* flesh together with *Akebia quinata* seeds and performing extraction, the extraction efficiency may be improved by up to 170%, as compared with the case of using only *Akebia quinata* seeds. Furthermore, when ginger is further added as an additive to be aged together with *Akebia quinata* flesh and seeds, the extraction efficiency may be improved by at most 120%, as compared with the case of extracting *Akebia quinata* feeds and flesh. That is, when the raw material contains *Akebia quinata* flesh and seeds, and ginger, the extraction efficiency may be improved by at most 200%, as compared with the case of using only *Akebia quinata* seeds. Cause of this phenomenon has not been also clearly revealed, but it is assumed that a certain component of ginger destroys a cell membrane of *Akebia quinata* seeds to improve the extraction efficiency of saponin. Type of ginger contained as the raw material may be exemplified by dried ginger powder, ginger pieces, crushed ginger, ginger juice or the like, but not limited thereto.

According to an exemplary embodiment of the present invention, the raw material may contain 0.05 to 0.2 parts by weight, preferably 0.07 to 0.13 parts by weight, more preferably 0.08 to 0.12 parts by weight of ginger, based on 1 part by weight of the Akebia quinata seeds. In order to show improvement of the saponin extraction efficiency from the Akebia quinata seeds, it is preferred to add 0.05 parts by weight or more of ginger, based on 1 part by weight of the Akebia quinata seeds, and when too much ginger is added, the extraction efficiency is not further improved, and rather the extraction may be interrupted, and thus, it is preferred to add 0.2 parts by weight or less of ginger.

Further, the aging temperature in the aging step of the present invention may be 20 to 60° C., preferably 30 to ° C., more preferably 35 to 45° C. When the aging temperature of the raw material containing Akebia quinata is 40° C., the extraction efficiency may be improved by 200% or more, as compared with the case of aging at less than ° C. It is seen therefrom that the effect of akebia quinata flesh or ginger on Akebia quinata seeds significantly depends on the temperature.

The aging of the present invention may be performed in purified water at 2 to 10 times weight of the raw material, but not limited thereto. Further, the alcohol extraction solution refers to C1 to C4 alcohol or a solution including 50 to 95 wt % of C1 to C4 alcohol and remaining water. Preferably, it refers to a solution including 50 to 90 wt % of ethanol or methanol and remaining water, and more preferably a solution including 70 to 90 wt % of ethanol and remaining water.

In the extraction from Akebia quinata according to another exemplary embodiment of the present invention, step b) may include:

b1) adding an alcohol extraction solution to the raw material aged in step a), and then performing ultrasonic irradiation; and b2) centrifuging a product from step b1) and recovering a supernatant liquid to prepare an extract, and the residue from which the supernatant liquid of step b2) is removed may be used as the raw material of step b1), thereby repeating steps b1) and b2) once or twice or more, after adding an alcohol extraction solution. Preferably the process may be repeated twice.

As a result of further study in order to improve the saponin extraction efficiency from Akebia quinata seeds, the extraction efficiency from Akebia quinata seeds was improved by performing ultrasonic irradiation when extracting using an extraction solution, as a method for improving extraction efficiency from Akebia quinata seeds. Generally, when performing extraction from a plant using ultrasonic waves, the ultrasonic irradiation may be carried out for 3 to 72 hours. However, it is effective that the ultrasonic irradiation of the present invention is carried out for 20 to 60 minutes, preferably 30 to 50 minutes. Specifically, when performing extraction from akebia quinata seeds, efficiency improvement was achieved with ultrasonic irradiation by at most 330%, as compared with the case without ultrasonic irradiation. More specifically, in the case of ultrasonic irradiation for 20 minutes, the extraction efficiency was improved by at most 270%, in the case of ultrasonic irradiation for 40 minutes, the extraction efficiency was improved by 310%, and in the case of ultrasonic irradiation for 60 minutes, the extraction efficiency was improved by 330%. It is seen therefrom that the ultrasonic irradiation time significantly influences the saponin extraction efficiency from Akebia quinata seeds. When performing ultrasonic irradiation for less than 10 minutes, the saponin extraction efficiency may not be improved, and when performing ultrasonic irradiation for 60 minutes or more, other effective components of the extract may be destroyed. Further, the ultrasonic waves according to an exemplary embodiment of the present invention may be at 10 to 50 kHz. When the ultrasonic waves are at less than 10 kHz, the extraction efficiency may not be improved, and when the ultrasonic waves are at more than 50 kHz, other effective components in the extract may be destroyed.

Furthermore, when performing extraction by adding an alcohol extraction solution again to the residue from which a supernatant liquid is removed after centrifuging, saponin remaining in the residue to be discarded may be utilized.

Further, the effective component of an Akebia quinata extract according to the present invention is saponin D, specifically "Pulsatilla saponin D" represented by the following Chemical Formula 1:

[Chemical Formula 1]

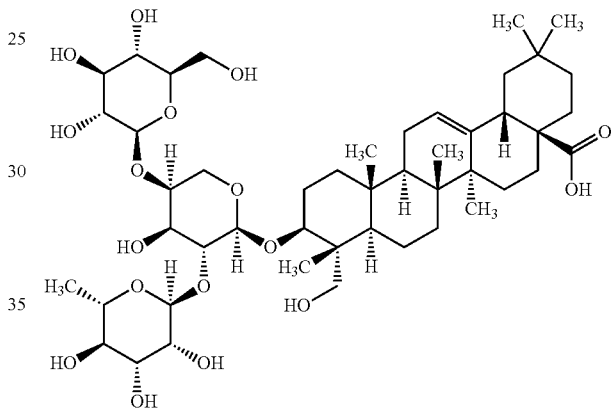

In the extraction from Akebia quinata according to an exemplary embodiment of the present invention, the extraction may be of course, additionally performed after aging, by further including other plants. Specifically, one or two or more selected from the group consisting of ginseng, wild ginseng, balloonflower, deodeok, kadzu and yam may be included. When plants such as ginseng, wild ginseng, balloonflower, deodeok, kadzu and yam are further added, and aging and extraction are performed, the effective components contained in the plants may be taken together with an Akebia quinata extract, thereby manufacturing food having further improved functionality.

The Akebia quinata extract according to the present invention may be taken as the extract itself, or granulated or capsulated to be taken, or used as an additive of other food, and when it is used as an additive of other food, it may be properly used according to a general method. When the Akebia quinata extract is used as an additive, it may be added at 0.01 to 50 wt % to the food, but the added amount may be properly adjusted depending on the use purpose.

The food to which the Akebia quinata extract according to the present invention is added is not particularly limited, and the specific example thereof includes meat, sausages, ham and other processed meat, chocolate, candy, snacks, confectionery, bread, pizza, ramen and other noodles, gums, dairy products including ice cream, beverages, tea, drinks, alcoholic beverages, multivitamin preparations, and the like.

Among the health functional food according to the present invention, the beverage may contain various flavors, natural carbohydrates or the like as an additional component, like common beverages. The natural carbohydrates may be monosaccharides such as glucose and fructose, disaccharides such as maltose and sucrose, polysaccharides such as dextrin and cyclodextrin, or sugar alcohols such as xylitol, sorbitol and erythritol.

Hereinafter, the present invention will be described in detail by Examples. The following Examples are specific examples for helping to understand the invention, and the present invention is not limited to the following Examples.

[Example 1] Improved Saponin Extraction Efficiency Depending on *Akebia Quinata* Flesh Powder Ratio 1 g of *Akebia quinata* seed powder was mixed with 0 g (Comparative Example 1), 0.3 g (Example 1-1), 0.5 g (Example 1-2), 0.7 g (Example 1-3), 1.0 g (Example 1-4), 1.5 g (Example 1-5), and 2.0 g (Example 1-6) of *akebia quinata* flesh powder, respectively, and the mixtures were added to 10 ml of purified water, and aged at 45° C. for 5 hours. 20 ml of an extraction solution of 80 wt % of ethanol and 20 wt % of water were added thereto, and ultrasonic irradiation was performed at 30 kHz with stirring for 30 minutes. Thereafter, centrifuge was performed at 3000 rpm for 20 minutes, and a supernatant liquid was recovered therefrom to prepare a first extract. 30 ml of the extraction solution was further added to the residue from which the supernatant liquid was removed, and ultrasonic irradiation was performed at 30 kHz while stirring for 30 minutes, and after centrifuging, the supernatant liquid was recovered to prepare a second extract. The first extract and the second extract were mixed, dried under reduced pressure, dissolved in 100 ml of purified water, and lyophilized. Thereafter, high performance liquid chromatography (Waters, Waters 2695 HPLC system) was used to measure the content of saponin, and the result is shown in Table 1:

TABLE 1

|  | *Akebia quinata* seed powder | *Akebia quinata* flesh powder | Saponin content |
|---|---|---|---|
| Comparative Example 1 | 1 g | 0 g | 5.27 mg |
| Example 1-1 | 1 g | 0.3 g | 6.52 mg |
| Example 1-2 | 1 g | 0.5 g | 7.45 mg |
| Example 1-3 | 1 g | 0.7 g | 8.26 mg |
| Example 1-4 | 1 g | 1.0 g | 8.68 mg |
| Example 1-5 | 1 g | 1.5 g | 8.49 mg |
| Example 1-6 | 1 g | 2.0 g | 8.37 mg |
| Example 1-7 | 1 g | 3.0 g | 8.21 mg |

[Example 2] Improved Saponin Extraction Efficiency Using Ginger 1 g of *Akebia quinata* seed and 1 g of *Akebia quinata* flesh were mixed with 0 g (Example 2-1), 0.03 g (Example 2-2), 0.05 g (Example 2-3), 0.1 g (Example 2-4), 0.15 g (Example 2-5), 0.2 g (Example 2-6) and 0.3 g (Example 2-7) of ginger, respectively, and the experiment was carried out in the same manner as in Example 1 to measure the content of saponin, and then the result is shown in Table 2:

TABLE 2

|  | *Akebia quinata* seed powder | *Akebia quinata* flesh powder | Ginger powder | Saponin content |
|---|---|---|---|---|
| Example 2-1 | 1 g | 1 g | 0 g | 8.68 mg |
| Example 2-2 | 1 g | 1 g | 0.03 g | 8.79 mg |
| Example 2-3 | 1 g | 1 g | 0.05 g | 9.63 mg |
| Example 2-4 | 1 g | 1 g | 0.10 g | 9.75 mg |
| Example 2-5 | 1 g | 1 g | 0.15 g | 9.84 mg |
| Example 2-6 | 1 g | 1 g | 0.20 g | 9.56 mg |
| Example 2-7 | 1 g | 1 g | 0.30 g | 9.12 mg |

[Example 3] Improved Saponin Extraction Efficiency Depending on Aging Temperature A mixture of 5 g of *Akebia quinata* seed powder and 5 g of *Akebia quinata* flesh powder was added to 50 ml of purified water, and aged at 20° C. (Example 3-1), 25° C. (Example 3-2), 30° C. (Example 3-3), 35° C. (Example 3-4), 40° C. (Example 3-5), 45° C. (Example 3-6), 50° C. (Example 3-7), 55° C. (Example 3-8), and 60° C. (Example 3-9) for 5 hours, respectively. 70 ml of an extraction solution of 80 wt % of ethanol and 20 wt % of water was added thereto, and ultrasonic irradiation was performed at 30 kHz for 30 minutes. Thereafter, centrifuge was performed at 3000 rpm for 20 minutes, and a supernatant liquid was recovered therefrom to prepare a first extract. 100 ml of the extraction solution was further added to the residue from which the supernatant liquid was removed, and ultrasonic irradiation was performed at 30 kHz with stirring for 30 minutes, and after centrifuging, the supernatant liquid was recovered to prepare a second extract. The first extract and the second extract were mixed, dried under reduced pressure, dissolved in 400 ml of purified water, and lyophilized. Thereafter, high performance liquid chromatography was used to measure the content of saponin.

TABLE 3

|  | Aging temperature | Saponin content |
|---|---|---|
| Example 3-1 | 20° C. | 35.9 mg |
| Example 3-2 | 25° C. | 47.3 mg |
| Example 3-3 | 30° C. | 59.5 mg |
| Example 3-4 | 35° C. | 68.7 mg |
| Example 3-5 | 40° C. | 73.2 mg |
| Example 3-6 | 45° C. | 70.2 mg |
| Example 3-7 | 50° C. | 62.3 mg |
| Example 3-8 | 55° C. | 54.9 mg |
| Example 3-9 | 60° C. | 47.6 mg |

[Example 4] Improved Saponin Extraction Efficiency Depending on Ultrasonic Irradiation Duration Extraction was performed at an aging temperature of 40° C. in the same manner as in Example 3, except that the ultrasonic irradiation duration in a first extract preparation process and a second extract preparation process is 0 minutes (Example 4-1), 10 minutes (Example 4-2), 20 minutes (Example 4-3), 30 minutes (Example 4-4), 40 minutes (Example 4-5), 50 minutes (Example 4-6), 60 minutes (Example 4-7), and 70 minutes (Example 4-8), respectively. The saponin contents by Examples are shown in Table 4:

TABLE 4

|  | Ultrasonic irradiation duration | Saponin content |
| --- | --- | --- |
| Example 4-1 | 0 min | 24.4 mg |
| Example 4-2 | 10 min | 37.4 mg |
| Example 4-3 | 20 min | 67.0 mg |
| Example 4-4 | 30 min | 73.2 mg |
| Example 4-5 | 40 min | 75.8 mg |
| Example 4-6 | 50 min | 77.3 mg |
| Example 4-7 | 60 min | 81.5 mg |
| Example 4-8 | 70 min | 82.7 mg |

[Experimental Example 1] Examination of Functionality of Akebia Quinata Extract

The extracts dried in Comparative Example 1, and Examples 1-4, 2-4 and 5 (further including 0.5 g of ginseng powder, Example 5) were prepared by the preparation method of the extracts, and given to 50 trained panels in their 20s to 40s at 100 mg each. After taking it, they evaluated flavor and taste characteristics, based on 5-point scale (1: extremely dislike or very strong, 2: dislike, 3: average, 4: satisfied or good, 5: very satisfied or very good), and the average values are shown in Table 5:

TABLE 5

|  | Overall likeli-hood | Bitter | Sweet | Sour | Acerbic | Refresh-ment | Unique odor |
| --- | --- | --- | --- | --- | --- | --- | --- |
| Comparative Example 1 | 2 | 1 | 1.3 | 2 | 2.2 | 2.2 | 1.2 |
| Example 1-4 | 3.1 | 3 | 4 | 1.7 | 2.3 | 2.3 | 2.2 |
| Example 2-4 | 4.5 | 3.6 | 4.6 | 2.4 | 2.7 | 4.1 | 4.2 |
| Example 5 | 4.6 | 3.7 | 4.6 | 3 | 3 | 4.2 | 4.3 |

[Experimental Example 2] Vitality Promotion Effect of Akebia Quinata Extract

The extract of Example 2-4 was given to a total of 30 people in their 20s to 50s, 15 males and 15 females, each at 100 mg twice a day for 10 days, and in order to compare the vitality promotion effect, a fatigue recovery degree was evaluated based on 5-point scale (5: very good, 4: good, 3: no difference, 2: bad, 1: very bad). As a result, it was confirmed that the average value was 4, and the standard deviation was 0.73, and thus, it is recognized therefrom that it has the fatigue recovery effect.

[Experimental Example 3] Cold Prevention or Cold Symptom Relief Effect of Akebia Quinata Extract An experimental group taking 10 mg of the extract of Example 2-4 daily, and a control group taking 10 mg of placebo made of flour daily were set, and the experiment was carried out for 1 year. The number of cold occurrence and cold lasting days in the experimental group and the control group for one year were indicated, which were shown in Table 6. Here, cold refers to the state representing two or more symptoms such as low fever or high fever, sore throat, cough, muscle aches and chills.

TABLE 6

|  | Experimental group | Control group |
| --- | --- | --- |
| Number of cold occurrence | 2.6 | 5.3 |
| Cold lasting days per number | 2.7 | 8.7 |

[Experimental Example 4] Stomach Discomfort Mitigation Effect of Akebia Quinata Extract The extract of above Example 2-4 was evaluated by 10 people who complained of stomach discomfort such as heartburn and acid reflux, for an improvement degree of heartburn, retching and gastric regurgitation symptoms, based on 5-point scale (1: much worse, 2: worse, 3: no change, 4: improved, 5: much improved), after they took 0.1 g of the extract twice a day for a month. As a result, for heartburn, the average was 4.4 and the standard deviation was 0.69, and for retching and gastric regurgitation, the average was 4.0 and the standard deviation was 0.94.

[Preparation Example 1] Preparation of Akebia Quinata Extract Tablets 150 mg of the extract of Example 2-4, 50 mg of crystalline cellulose, 50 mg of lactose, 3 mg of magnesium stearate and ethanol were mixed and granules were prepared therefrom.

[Preparation Example 2] Preparation of Akebia Quinata Extract Capsules 200 mg of the extract of Example 2-4, 10 mg of talc, 5 mg of colloid silica, and 85 mg of lactose were prepared into capsules by a general preparation method of capsules.

[Preparation Example 3] Preparation of Akebia Quinata Extract Drinks 4 g of the extract of Example 2-4, 0.5 g of oligosaccharide, 1 g of high fructose corn syrup, 0.1 g of citric acid, 0.2 g of vitamin C, and 50 ml of purified water were mixed and prepared into drinks by a common preparation method of drinks.

The method of extracting from Akebia quinata according to the present invention may improve the saponin extraction efficiency from Akebia quinata seeds by using Akebia quinata flesh, and further improve the saponin extraction efficiency from Akebia quinata seeds by using ginger. Further, health functional food having improved functionality may be accordingly provided.

What is claimed is:
1. A method of preparing an Akebia quinata extract comprising
  (a) aging raw material in water for at least 5 hours at 20-60° C.;
  (b) adding a C1-C4 alcohol to the water to produce a hydroalcoholic extraction solvent to produce an extraction solution;
  (c) performing ultrasonic irradiation on the extraction solution for 20 to 60 minutes; and
  (d) centrifuging the solution to produce a residue and recovering a supernatant liquid to obtain said Akebia quinata extract, wherein the raw material comprises *Akebia quinata* seeds and *Akebia quinata* flesh and ginger at a ratio of 1 to 1-1.5 to 0.05-0.2,
wherein the extract comprises an effective amount of *Pulsatilla* saponin D.

2. The method of claim 1, wherein the raw material further includes 0.1 to 1 part by weight of one or two or more additives selected from the group consisting of ginseng, wild ginseng, balloonflower, deodeok, kadzu and yam, based on 1 part by weight of the *akebia quinata* seeds.

3. The method of claim 1, further comprising the steps of using the residue of step (d) and repeating steps (b)-(d) twice or more.

\* \* \* \* \*